(12) United States Patent
Pillai et al.

(10) Patent No.: US 9,220,874 B2
(45) Date of Patent: Dec. 29, 2015

(54) TRANSVASCULAR ACCESS DEVICE AND METHOD

(71) Applicants: Lakshmikumar Pillai, Morgantown, WV (US); Patrick Burt, Palo Alto, CA (US); John Lunsford, Los Altos, CA (US); John Stiggelbout, Sausalito, CA (US)

(72) Inventors: Lakshmikumar Pillai, Morgantown, WV (US); Patrick Burt, Palo Alto, CA (US); John Lunsford, Los Altos, CA (US); John Stiggelbout, Sausalito, CA (US)

(73) Assignee: Vascular Access Technologies, Inc., Palo Alto, CA (US)

(*) Notice: Subject to any disclaimer, the term of this patent is extended or adjusted under 35 U.S.C. 154(b) by 0 days.

(21) Appl. No.: 13/906,122

(22) Filed: May 30, 2013

(65) Prior Publication Data

US 2013/0324967 A1 Dec. 5, 2013

Related U.S. Application Data

(60) Provisional application No. 61/653,182, filed on May 30, 2012.

(51) Int. Cl.
*A61M 25/09* (2006.01)
*A61M 25/00* (2006.01)
(Continued)

(52) U.S. Cl.
CPC ............ *A61M 25/09* (2013.01); *A61M 25/0082* (2013.01); *A61B 17/3415* (2013.01); *A61M 25/01* (2013.01); *A61M 25/09041* (2013.01); *A61M 2025/0095* (2013.01)

(58) Field of Classification Search
CPC ............ A61M 25/09; A61M 25/0082; A61M 25/09041; A61M 2025/0095; A61M 25/01; A61B 17/3415
USPC .......... 604/95.04, 164.01, 272, 528; 606/167, 606/170, 172, 185
See application file for complete search history.

(56) References Cited

U.S. PATENT DOCUMENTS 4,559,039 A 12/1985 Ash et al.
4,790,825 A 12/1988 Bernstein et al.
(Continued)

FOREIGN PATENT DOCUMENTS

WO WO 2004/018029 A2 3/2004
WO WO 2005/053547 A2 6/2005
(Continued)

OTHER PUBLICATIONS

Faul et al.; Vascular Disease Management; vol. 5; No. 5; pp. 128-133; Sep./Oct. 2008.
(Continued)

*Primary Examiner* — Theodore Stigell
(74) *Attorney, Agent, or Firm* — Shay Glenn LLP

(57) ABSTRACT

Transvascular access devices and methods for transvascular access are provided. The transvascular access devices can include a guidewire lumen and a guide tube and stylet disposed in a second lumen. The guide tube can be used to control the orientation of the stylet and provide additional support for the stylet. The methods include providing a second entry point in a vessel of a patient remote from a first entry point. A vascular catheter can enter the vascular system of a patient at a first entry point and be advanced to a second entry point. A guide tube can be advanced out the second lumen of the vascular catheter with a stylet advanced out of the guide tube to pierce the vessel wall and skin of the patient at the second entry point. A catheter can be introduced to the vascular system at the second entry point.

13 Claims, 18 Drawing Sheets

(51) Int. Cl.
*A61M 25/01* (2006.01)
*A61B 17/34* (2006.01)

(56) References Cited

U.S. PATENT DOCUMENTS

| | | | |
|---|---|---|---|
| 4,966,163 A | 10/1990 | Kraus et al. | |
| 5,421,348 A | 6/1995 | Larnard | |
| 5,492,530 A | 2/1996 | Fischell et al. | |
| 5,685,820 A | 11/1997 | Riek et al. | |
| 5,733,248 A | 3/1998 | Adams et al. | |
| 6,047,700 A | 4/2000 | Eggers et al. | |
| 6,102,887 A * | 8/2000 | Altman | 604/22 |
| 6,102,926 A | 8/2000 | Tartaglia et al. | |
| 6,217,527 B1 | 4/2001 | Selmon et al. | |
| 6,475,226 B1 | 11/2002 | Belef et al. | |
| 6,508,777 B1 | 1/2003 | Macoviak et al. | |
| 6,554,794 B1 | 4/2003 | Mueller et al. | |
| 6,623,480 B1 | 9/2003 | Kuo et al. | |
| 6,726,677 B1 * | 4/2004 | Flaherty et al. | 604/528 |
| 6,955,657 B1 * | 10/2005 | Webler | 604/95.04 |
| 7,008,979 B2 | 3/2006 | Schottman et al. | |
| 7,374,567 B2 | 5/2008 | Heuser | |
| 7,648,517 B2 | 1/2010 | Makower et al. | |
| 8,019,420 B2 | 9/2011 | Hine et al. | |
| 8,241,311 B2 | 8/2012 | Ward et al. | |
| 8,374,680 B2 | 2/2013 | Thompson | |
| 8,409,236 B2 | 4/2013 | Pillai | |
| 2001/0012924 A1 | 8/2001 | Milo et al. | |
| 2001/0023346 A1 | 9/2001 | Loeb | |
| 2002/0004666 A1 | 1/2002 | Schwager et al. | |
| 2002/0029060 A1 | 3/2002 | Hogendijk | |
| 2002/0120250 A1 | 8/2002 | Altman | |
| 2002/0133168 A1 | 9/2002 | Smedley et al. | |
| 2002/0169377 A1 | 11/2002 | Khairkhahan et al. | |
| 2004/0039371 A1 | 2/2004 | Tockman et al. | |
| 2004/0059280 A1 | 3/2004 | Makower et al. | |
| 2004/0082850 A1 | 4/2004 | Bonner et al. | |
| 2004/0133168 A1 | 7/2004 | Salcudean et al. | |
| 2004/0181150 A1 * | 9/2004 | Evans et al. | 600/433 |
| 2004/0181238 A1 | 9/2004 | Zarbatany et al. | |
| 2005/0101984 A1 | 5/2005 | Chanduszko et al. | |
| 2005/0149097 A1 | 7/2005 | Regnell et al. | |
| 2005/0209579 A1 | 9/2005 | Yacoubian et al. | |
| 2006/0009737 A1 | 1/2006 | Whiting et al. | |
| 2006/0135962 A1 | 6/2006 | Kick et al. | |
| 2006/0247750 A1 | 11/2006 | Seifert et al. | |
| 2007/0021767 A1 | 1/2007 | Breznock | |
| 2008/0082136 A1 | 4/2008 | Gaudini | |
| 2008/0125748 A1 | 5/2008 | Patel | |
| 2008/0154172 A1 | 6/2008 | Mauch | |
| 2008/0215008 A1 | 9/2008 | Nance et al. | |
| 2008/0249565 A1 | 10/2008 | Michler et al. | |
| 2009/0112050 A1 | 4/2009 | Farnan et al. | |
| 2009/0240122 A1 | 9/2009 | Avitsian | |
| 2010/0249491 A1 | 9/2010 | Farnan et al. | |
| 2011/0178530 A1 | 7/2011 | Bly | |
| 2011/0295206 A1 | 12/2011 | Gurley | |
| 2012/0136247 A1 | 5/2012 | Pillai | |
| 2012/0136366 A1 | 5/2012 | Pillai | |
| 2013/0006282 A1 | 1/2013 | Wilkinson | |
| 2013/0172922 A1 | 7/2013 | Pillai et al. | |
| 2014/0142418 A1 | 5/2014 | Gurley et al. | |

FOREIGN PATENT DOCUMENTS

| | | |
|---|---|---|
| WO | WO 2011/068540 A1 | 6/2011 |
| WO | WO 2013/119547 A1 | 8/2013 |

OTHER PUBLICATIONS

Huang et al.; Evaluation of the needle technique for producing an arteriovenous fistula; Journal of Applied Physiology; vol. 77(6); pp. 2907-2911; Dec. 1994.

Khanna et al.; Sharpening of hollow silicon microneedles to reduce skin penetration force; J. Micromech. Microeng.; vol. 20; No. 4, pp. 045011 (8 pgs.); Mar. 15, 2010.

LuMEND, Inc.; Outback LTD re-entry catheter; Product Resources (http://www.lumend.com/Images/Technology/Product/brochure.pdf) This web address was available to applicant(s) at least as of (Jul. 19, 2006).

Mewissen, Mark; Revascularization of long FP arterial occlusions; Endovascular Today; pp. 2-4; Mar. 2004.

O'Callaghan et al.; Dynamics of stab wounds: force required for penetration of various cadaveric human tissues; Forensic Sci. Int'l; vol. 104; pp. 173-178; Oct. 11, 1999.

Pillai, Lakshmikumar; U.S. Appl. No. 11/381,229 entitled "Methods of Transvascular Retrograde Access Placement and Devices for Facilitating Therein," filed May 2, 2006.

Pillai, Lakshmikumar; U.S. Appl. No. 13/904,876 entitled "Transvascular Access Methods," filed May 29, 2013.

* cited by examiner

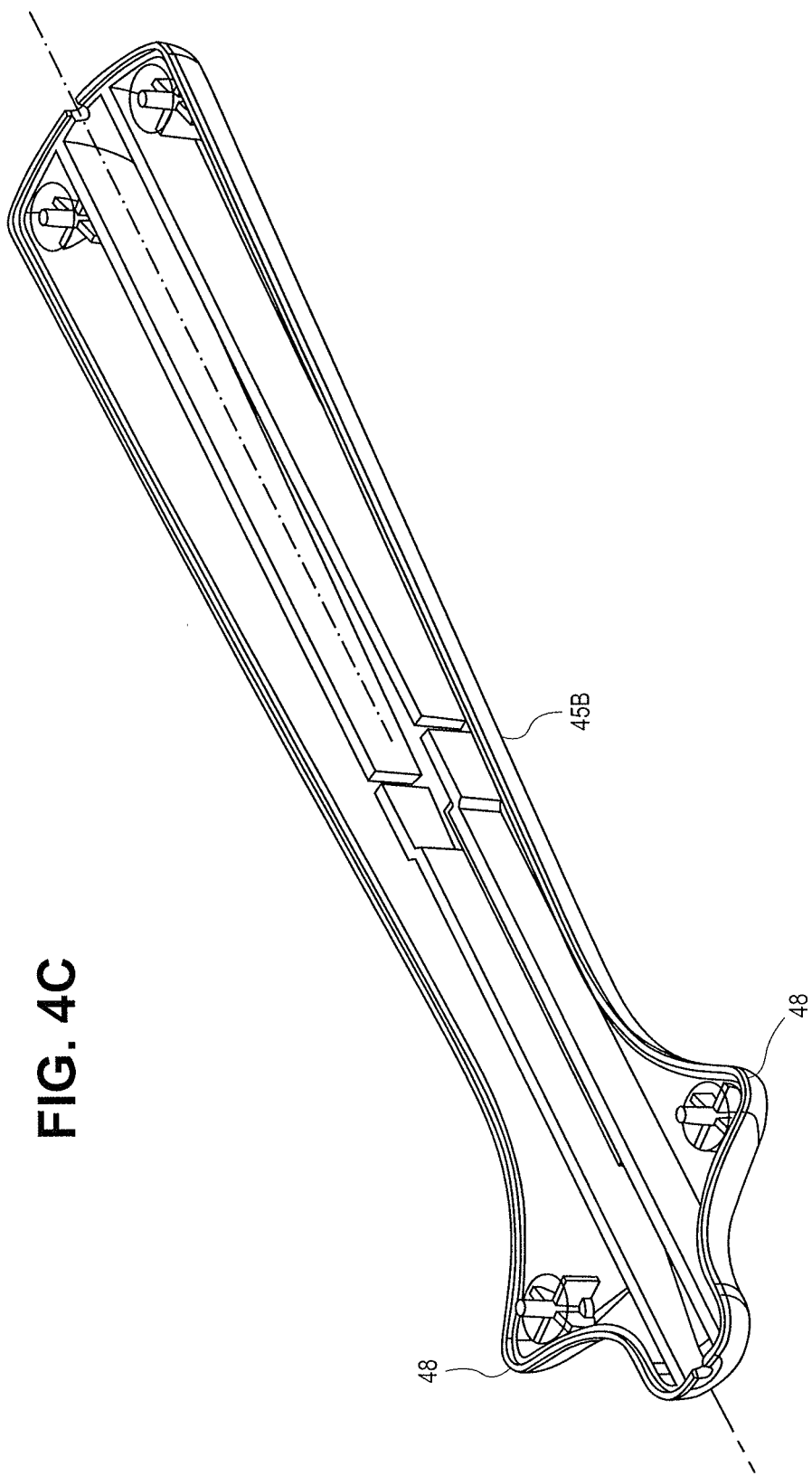

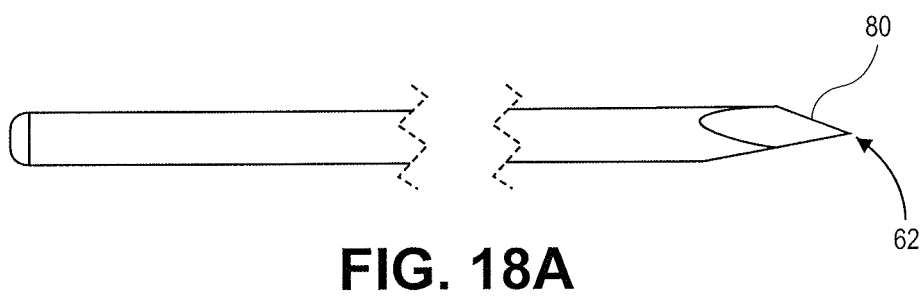
FIG. 18A
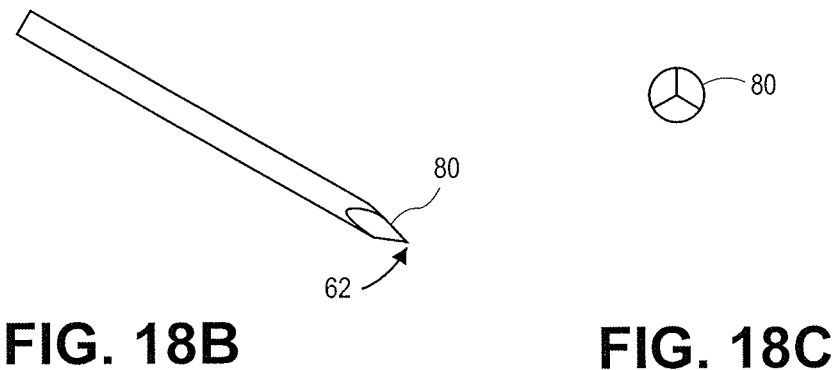
FIG. 18B  FIG. 18C

TRANSVASCULAR ACCESS DEVICE AND METHOD

CROSS REFERENCE TO RELATED APPLICATIONS

This application claims priority to U.S. Provisional Application No. 61/653,182, filed May 30, 2012, the disclosure of which is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The present invention relates to methods and devices for providing transvascular access to blood vessels. Prior devices and methods have been described for providing, e.g., access for placing a central venous line in the jugular vein using a remote vascular entry point, such as the femoral vein. In those prior approaches, a steerable catheter with a bent or bendable tip is guided from the femoral or other entry point to the desired central venous line entry point in the jugular vein. The tip of a sharp wire or stylet is then advanced out of the catheter and through the vessel wall and skin of the patient, and the central venous line is then inserted over the wire or stylet. More details of these prior devices and methods may be found in U.S. application Ser. No. 12/861,716 (filed Aug. 23, 2010); U.S. application Ser. No. 12/366,517 (filed Feb. 5, 2009); and U.S. application Ser. No. 11/424,131 (filed Jun. 14, 2006), the disclosures of which are incorporated herein by reference.

SUMMARY OF THE DISCLOSURE

The present invention provides new devices and methods for providing a second entry point to a vessel remote from a first entry point. One aspect of the invention provides a system for providing a second entry point in a vessel remote from a first entry point, including the following elements: a vascular catheter having first and second lumens, the first lumen being adapted to receive a vascular guidewire; a guide tube disposed in the second lumen, the guide tube having a distal end with a preformed curve; a stylet disposed in the guide tube, the stylet having a sharp distal tip adapted to pierce vascular tissue, muscle and skin; a guide tube actuator operatively connected to the guide tube or vascular catheter, the guide tube actuator configured to produce relative movement between the guide tube and the vascular catheter; and a stylet actuator operatively connected to the stylet, the stylet actuator having a stylet advancement mechanism. In some embodiments, the second lumen extends in a curve at its distal end.

In some embodiments, the guide tube actuator and the stylet actuator are supported by a handle at the proximal end of the vascular catheter. In some such embodiments, the guide tube actuator has a slider movably disposed in the handle and operatively connected to the guide tube or vascular catheter. In some embodiments the slider is operatively connected to the guide tube and is configured to advance the guide tube relative to the second lumen of the vascular catheter. In some embodiments the slider is operatively connected to the vascular catheter and configured to move the vascular catheter relative to the guide tube.

In some embodiments the handle includes a first wing and a second wing on opposing sides of the handle with the preformed curvature of the guide tube oriented to extend perpendicular relative to a plane defined by the first and second wings. In some embodiments the slider is on the same side of the handle as the side that the preformed curvature of the guide tube is oriented to extend towards.

In some embodiments, the sharp distal tip includes a conical shaped tip. In some embodiments the sharp distal tip includes a faceted tip.

In some embodiments, the stylet actuator includes a spring. In some such embodiments, the stylet actuator can also have a spring loading actuator and a spring release actuator.

Another aspect of the invention provides a method of providing a second entry point in a vessel of a patient remote from a first entry point. The method may include the following steps: deploying a vascular guidewire into the vessel from the first entry point toward the second entry point; inserting the guidewire into a first lumen of a vascular catheter; advancing the vascular catheter over the guidewire from the first entry point toward the second entry point; advancing a guide tube out of a distal end of a second lumen of the vascular catheter; directing a distal opening of the guide tube towards a wall of the vessel at the second entry point; and advancing a stylet out of the distal end of the guide tube, through the vessel wall and skin of the patient.

In some embodiments directing the distal opening of the guide tube towards the wall of the vessel at the second entry point includes placing the distal opening of the guide tube against the wall of the vessel at the second entry point.

Some embodiments also include the step of inserting a device over the stylet and into the vessel at the second entry point.

In some embodiments, the guide tube has a preformed curve at its distal end, and the step of advancing the guide tube includes the step of permitting the guide tube distal end to assume its preformed curve as the guide tube distal end is advanced out of the distal end of the second lumen of the vascular catheter.

In some embodiments, the second lumen of the vascular catheter extends in a curve at its distal end, and the step of advancing the guide tube includes the step of engaging a camming surface in the curve of the second lumen with a distal end of the guide tube to advance the distal end of the guide tube away from a longitudinal axis of the vascular catheter and toward a wall of the vessel.

In some embodiments, the step of advancing the guide tube includes the step of moving an actuator in a handle at the proximal end of the vascular catheter. In some embodiments moving the actuator advances the guide tube relative to the second lumen of the vascular catheter. In some embodiments moving the actuator proximally retracts the vascular catheter relative to the guide tube In some embodiments, the step of advancing the stylet includes the step of operating a stylet actuator in a handle at the proximal end of the vascular catheter. In some such embodiments, operation of the actuator releases a spring. The method may also include the step of loading the spring prior to the step of releasing the spring.

Some embodiments include verifying the positioning of the guide tube after placing the distal opening of the guide tube against the wall of the vessel at the second entry point prior to advancing the stylet. Verifying can include using fluoroscopy to verify the position of the guide tube.

Some embodiments include adjusting the orientation of the handle prior to advancing the guide tube to orient the vascular catheter such that when the guide tube is advanced out of the distal end of the second lumen, the guide tube extends from the vascular catheter towards the skin of the patient at the second entry point.

In some embodiments the first entry point is selected from the group consisting of: the femoral vein and femoral artery, and the second entry point is selected from the group consisting of: the internal jugular vein, subclavian vein, carotid artery, axillary artery, and subclavian artery.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4C is a perspective view of a cross section of the bottom of the device of FIG. 2.

FIG. 18A is a side-view of a faceted stylet tip in accordance with an embodiment. FIG. 18B is an isometric view of the device of FIG. 18A. FIG. 18C is an end view of the sharp distal point of the device of FIG. 18A.

DETAILED DESCRIPTION

Figure 1:
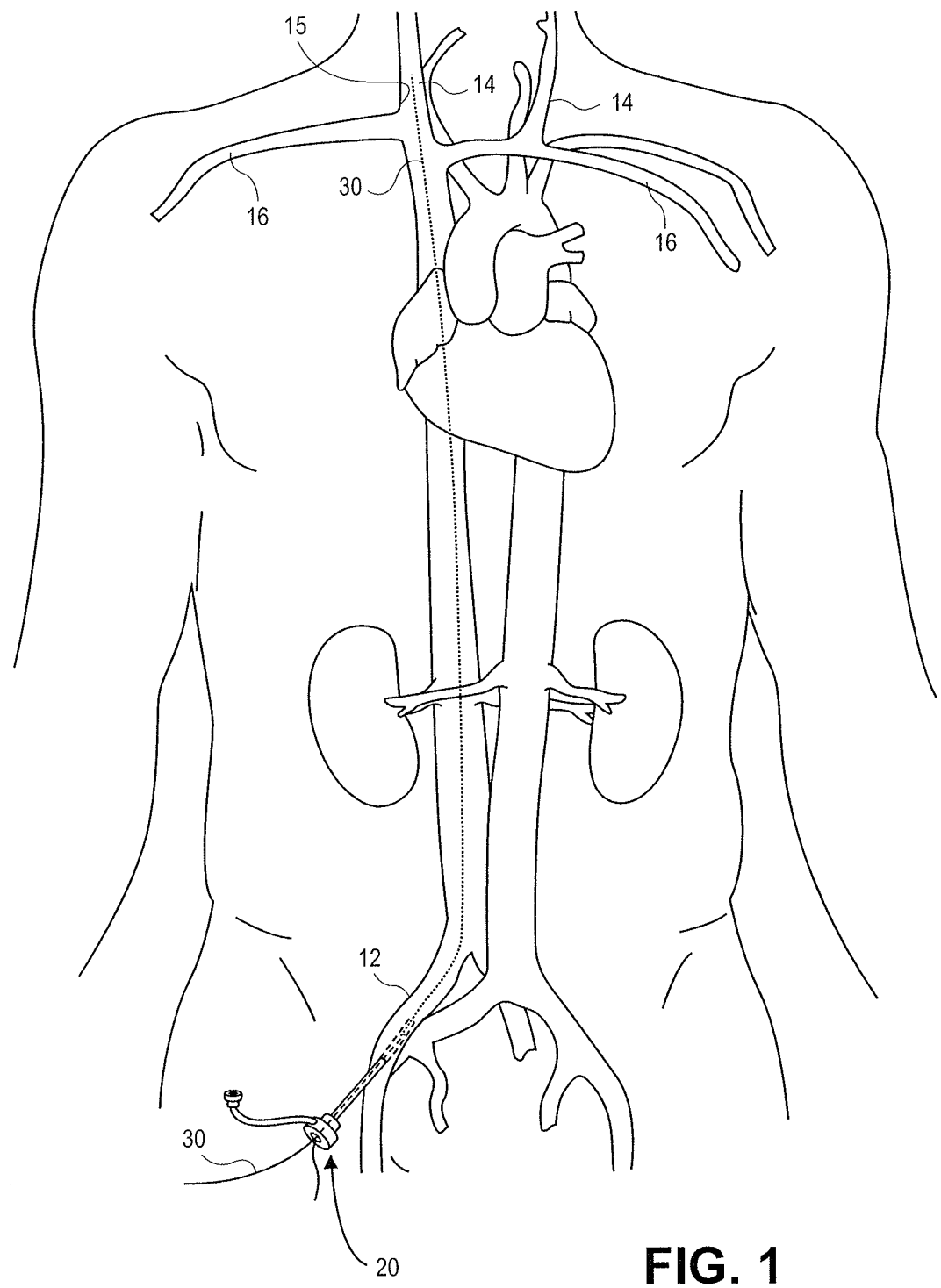
FIG. 1 is a schematic drawing illustrating the insertion of a guidewire extending from a patient's femoral vein to the jugular vein.
Figure 2:
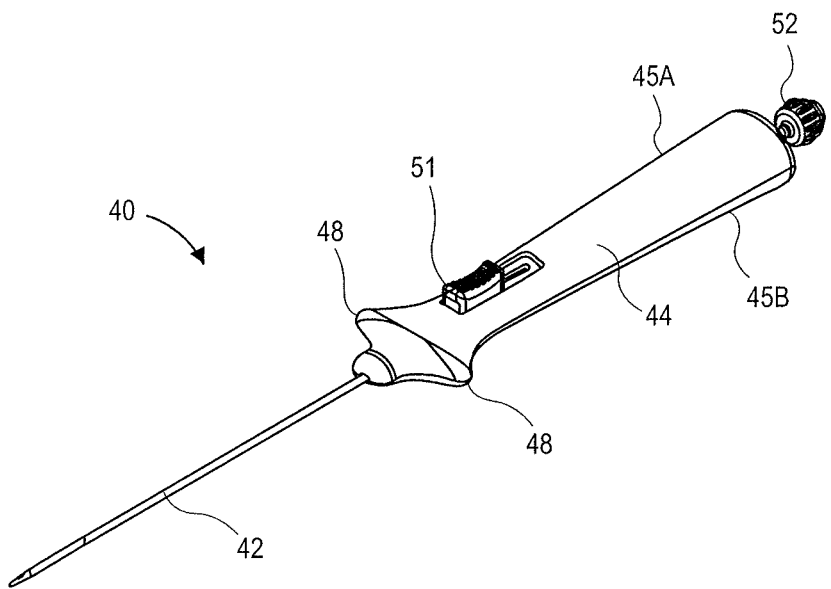
FIG. 2 is a perspective view of a transvascular access device according to an embodiment of the invention.
Figure 3:
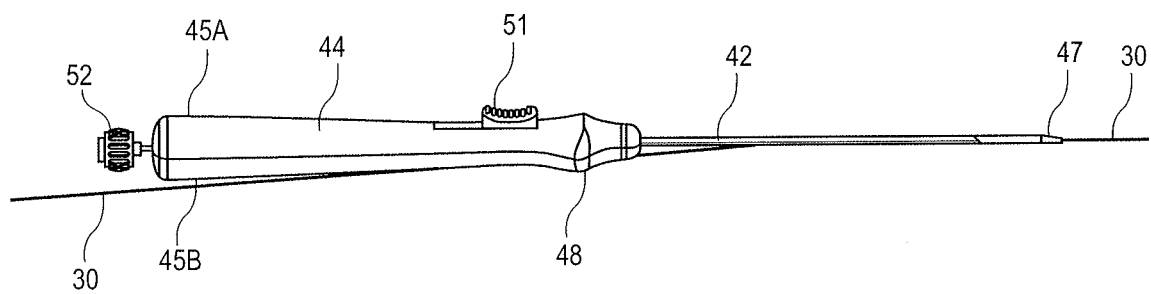
FIG. 3 is a side view of the device of FIG. 2 mounted on a guidewire.

FIG. 1 shows a patient whose femoral vein 12 has been accessed by the Modified Seldinger Technique. A general use guidewire 30 typically measuring about 0.035 inches in diameter has been passed through a vascular sheath 20 and ultimately positioned in a jugular vein 14 in the vicinity of a desired exit and reentry site (or pass-through site) 15 for central vein access.

FIGS. 2-17 show various embodiments of access devices. FIGS. 2-17 are not drawn to scale to facilitate the illustration of the device 40. A vascular catheter 42 extends from a handle 44. The length and diameter of catheter 42 depend on the distance between the remote first entry point and the desired second entry point. For example, if the remote entry point is the femoral vein and the desired second entry point is the jugular vein, as shown in FIG. 1, the vascular catheter may have a length of about 1 meter and may have a diameter of around 7 french (0.092 inches). The catheter may have a tapered or conical tip 47.

In some embodiments, the vascular catheter has an optional guidewire lumen. In the embodiments shown in FIGS. 2-17, the guidewire lumen 46 is configured as a rapid exchange (RX) guidewire lumen for receiving a guidewire 30. In embodiments in which the remote entry point is the femoral vein and the desired second entry point is the jugular vein, the guidewire 30 may be a 0.035 inch guidewire. In some embodiments the guidewire 30 is advanced through the handle 44 of the access device 40. In some embodiments the guidewire 30 can be introduced into the guidewire lumen 46 using an introducer kit (not shown). The guidewire can be positioned adjacent to the desired second entry point in the patient's vascular system. The vascular catheter can be advanced over the guidewire before or after the guidewire is positioned adjacent to the desired second entry point.

Figure 4A:
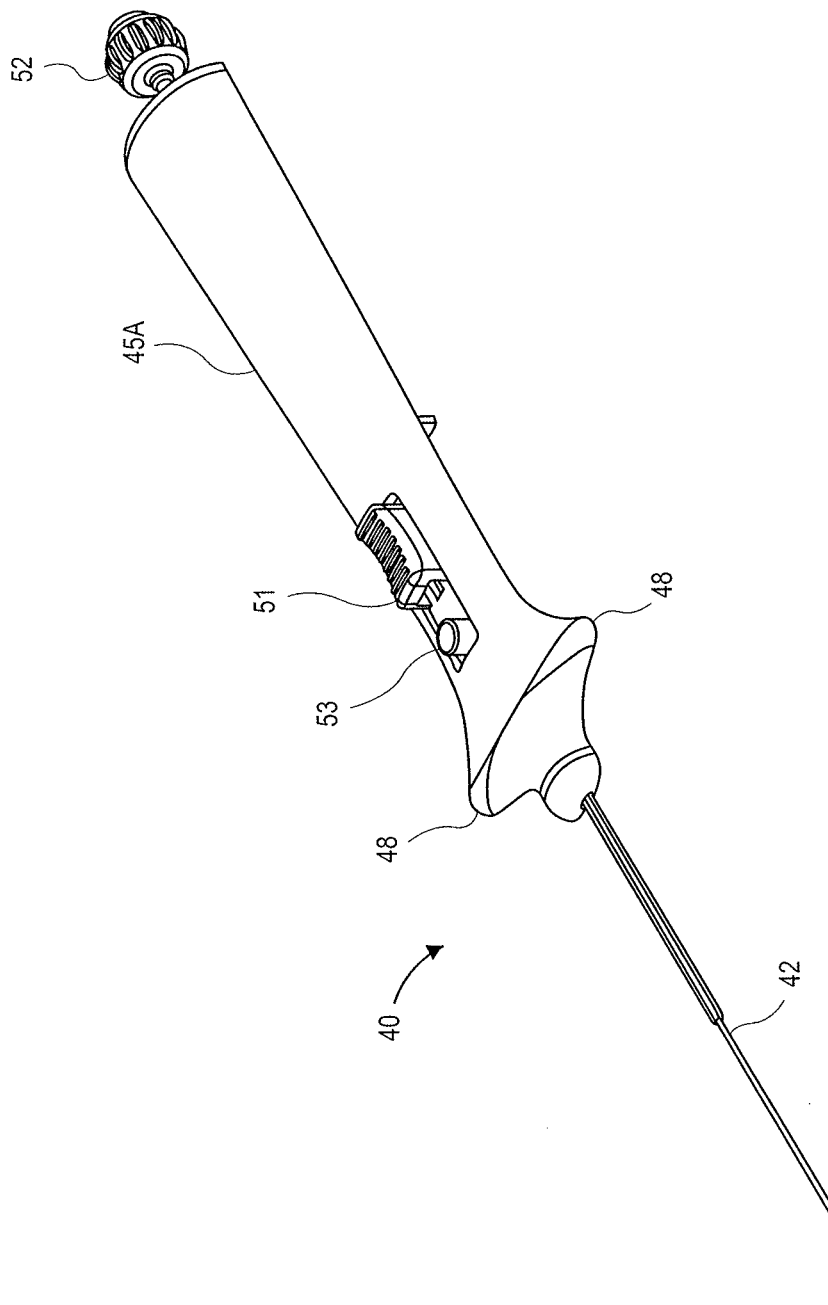
FIG. 4A is a perspective view of a cross section of the device of FIG. 2.
Figure 4B:
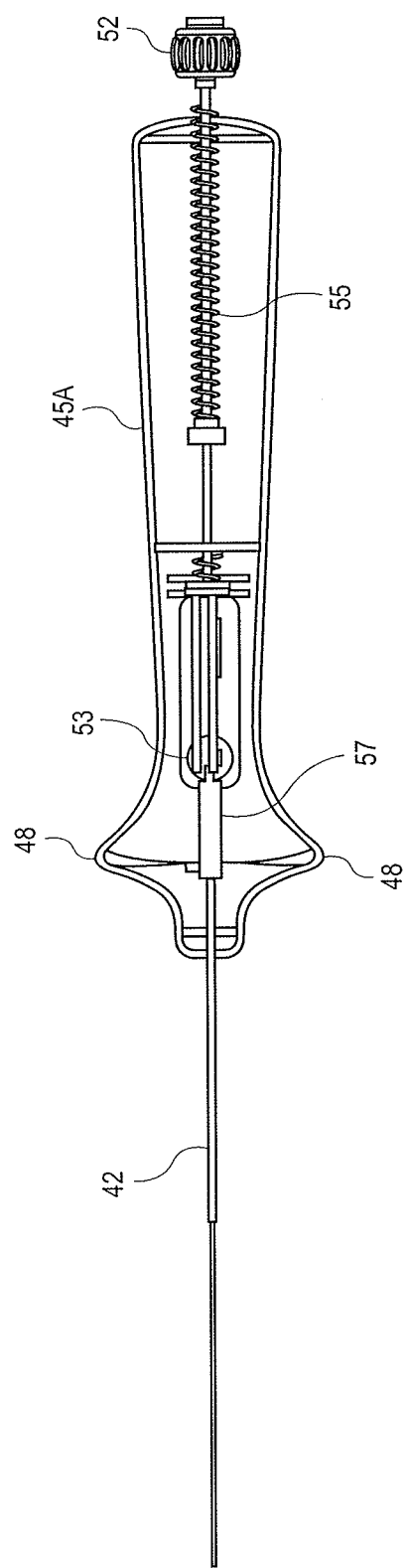
FIG. 4B is a bottom view of a cross section of the device of FIG. 2.

The handle 44 can include a top portion 45A and a bottom portion 45B. FIG. 4A illustrates a top of the top portion 45A of the handle 44. FIG. 4B illustrates a bottom of the top portion 45A of the handle 44. FIG. 4C illustrates a bottom portion 45B of the handle 44. The top portion 45A and bottom portion 45B can engage to form the handle 44. The handle 44 also includes wings 48 on opposing sides of the handle 44. The wings 48 can be used to apply a distal force to the vascular catheter from the handle.

Figure 6A:
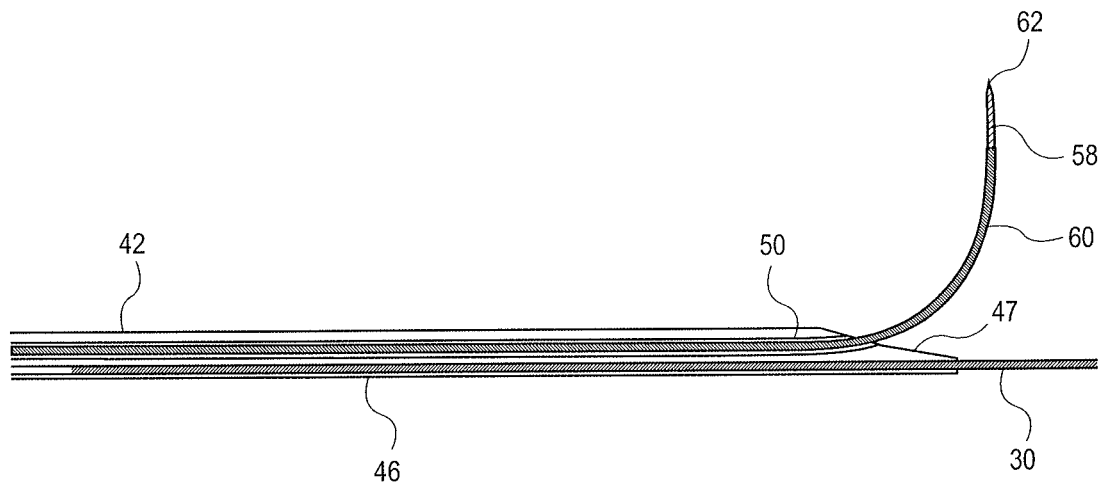
FIG. 6A is a cross-sectional schematic view of the device of FIG. 2 with the stylet deployed.
Figure 6B:
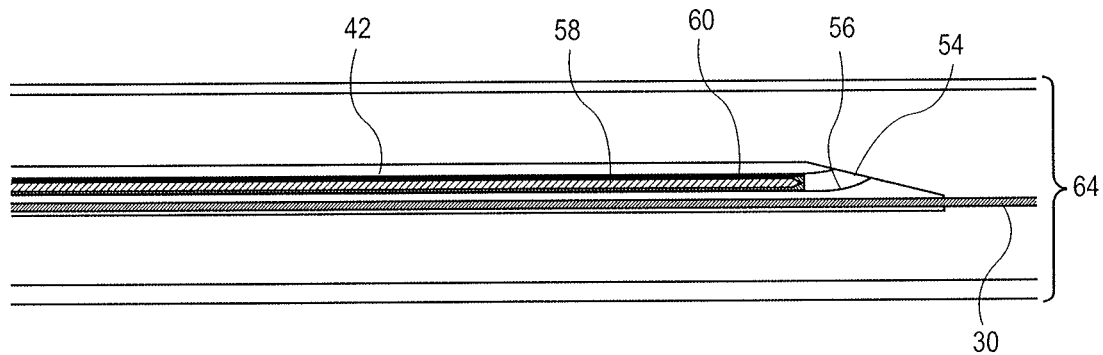
FIG. 6B is a cross-sectional schematic view of the device of FIG. 2 being advanced over a guidewire in a vessel, such as a vein.

In addition to the guidewire lumen 46, device 40 has a stylet lumen 50 extending from the handle 44 to an opening 54 toward the distal end of the catheter. In some embodiments, the stylet lumen curves at its distal end to form a camming surface 56. A curved stylet lumen with a camming surface 56 is shown in FIGS. 6A and 6B. The camming surface 56 can provide additional structural support to a guide tube or cover tube 60 when it is in an advanced position. A stylet 58 is slidably disposed within the cover tube 60.

Figure 7A:
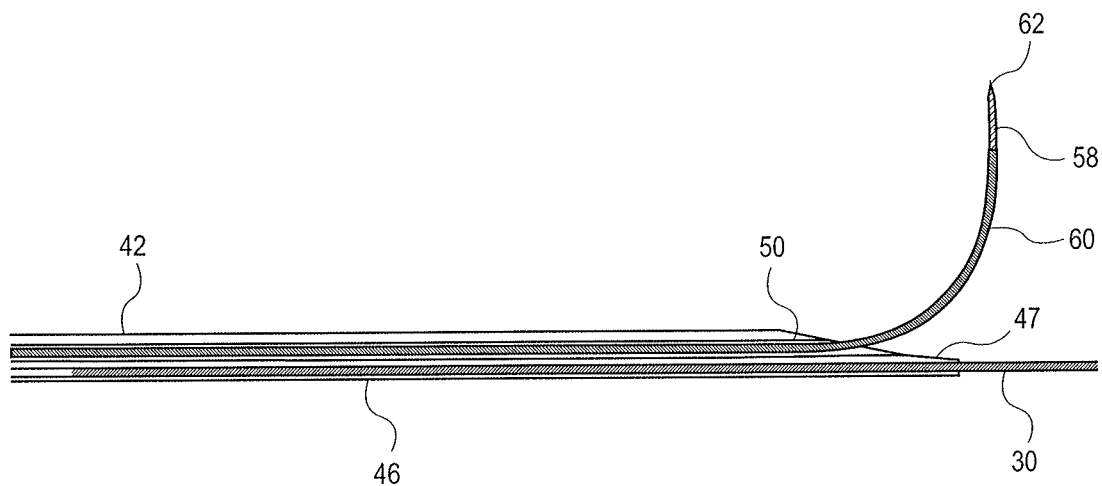
FIG. 7A is a cross-sectional schematic view of a device in accordance with an embodiment with the stylet deployed.
Figure 7B:
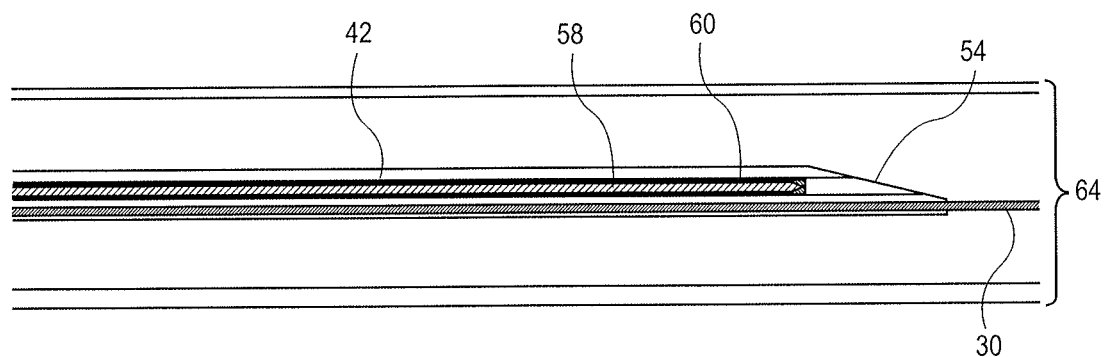
FIG. 7B is a cross-sectional schematic view of a device in accordance with an embodiment being advanced over a guidewire in a vessel, such as a vein.

In some embodiments the stylet lumen 50 does not have a curved camming surface. For example, the stylet lumen 50 can be substantially cylindrical as illustrated in FIGS. 7A and 7B.

The stylet 58 (formed, e.g., from Nitinol with a diameter of 0.014 inches) enclosed by the cover tube 60 (such as a 0.025 inch diameter Nitinol hypotube) extends from an actuator 51, 52 and 53 in the handle 44 toward the distal end of device 40. In some embodiments, cover tube 60 has a preformed curve, such as a 90 degree curve, at its distal end. The optional camming surface 56 can promote the curvature of the cover tube 60.

Figure 19A:
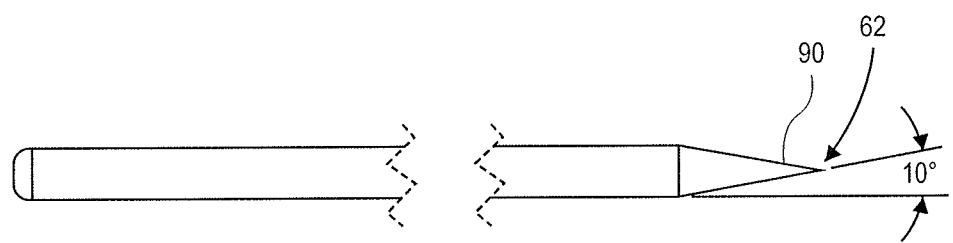
FIG. 19A is a side-view of a conical stylet tip in accordance with an embodiment.
Figure 19B:
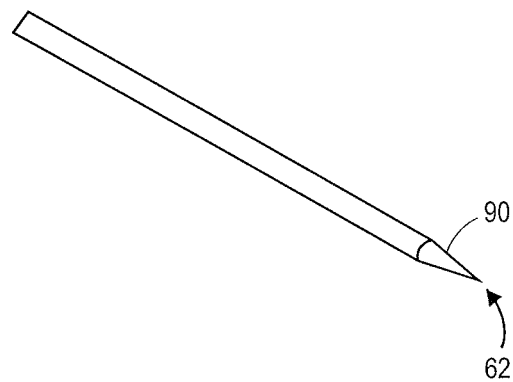
FIG. 19B is an isometric view of the device of FIG. 19A.

Stylet 58 has a sharp distal point 62 adapted to penetrate tissue, such as blood vessels, muscle, and skin. The sharp distal point can be part of a tip design having various dimensions and shapes. In some embodiments a faceted tip 80 is used. FIGS. 18A-18C illustrate various views of the faceted tip 80. The illustrated faceted tip 80 includes three flat surfaces that intersect to form the sharp distal point 62. In some embodiments a conical tip 90 is used. FIGS. 19A-19B illustrate various views of the conical tip 90. The illustrated conical tip 90 forms an angle of about 10° with the shaft of the stylet 58.

Figure 8:
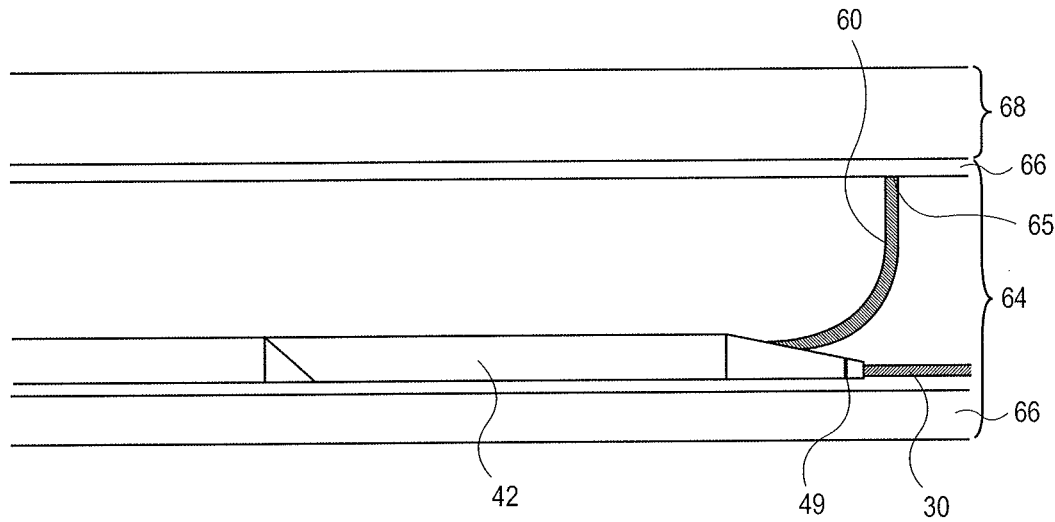
FIG. 8 is a cross-sectional schematic view of the device of FIG. 2 with the stylet cover tube advanced to a desired exit point within the vessel.

In use, e.g., to provide a jugular vein second entry point using the femoral vein as a first entry point, catheter 40 is inserted into the femoral vein over the guidewire 30 and advanced adjacent to the desired exit point 65 (FIG. 8) in the jugular vein 64 under fluoroscopic guidance with the stylet and cover tube in a retracted position, as shown in FIG. 6B, and the distal opening of the stylet lumen is oriented toward the desired exit point 65 in the vein wall 66. In some embodiments the catheter tip 47 includes a radiopaque marker 49 visible under fluoroscopy as shown in FIG. 8. The radiopaque marker 49 can be embedded in the catheter tip 47. The radiopaque marker 49 is illustrated as a ring in FIG. 8; however, other shapes and geometries can be used. In some embodiments the shape of the radiopaque marker can be selected to facilitate fluoroscopic identification of the location and orientation of the catheter tip 47. Examples of radiopaque marker materials include gold, platinum, platinum-iridium, and other biocompatible radiopaque materials.

Figure 5A:
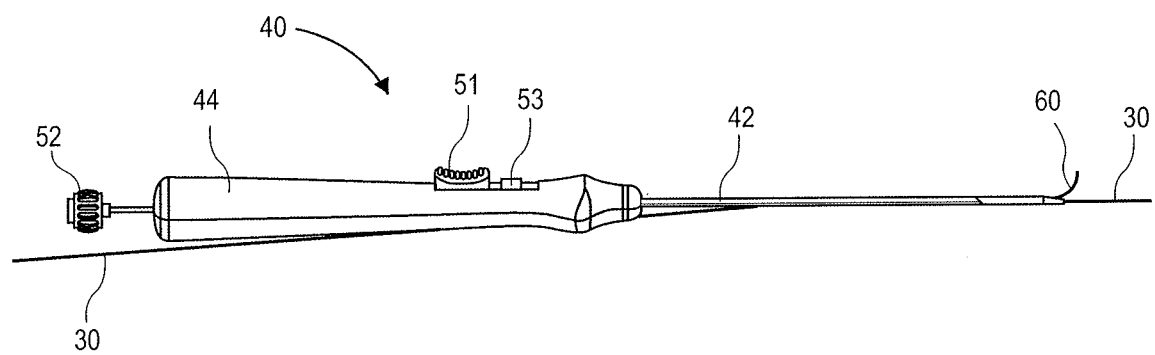
FIG. 5A is a side view of the device of FIG. 2 with the stylet cover tube advanced and the stylet actuator loaded.
Figure 5B:
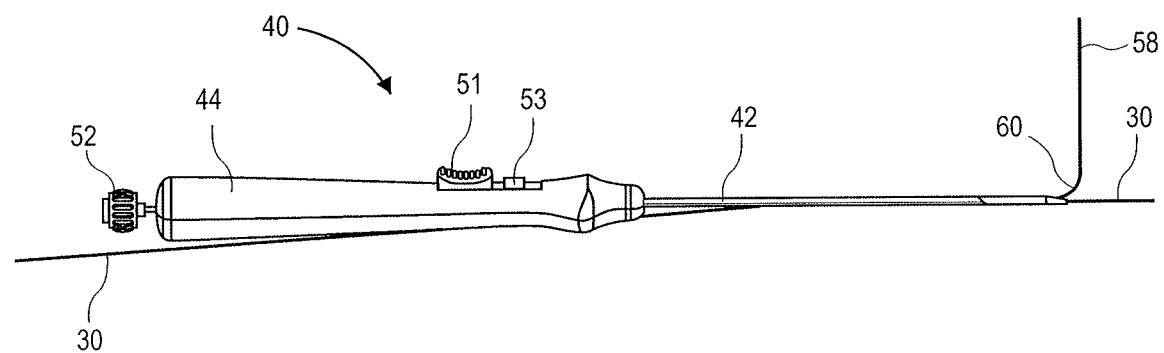
FIG. 5B is a side view of the device of FIG. 2 with the stylet deployed.
Figure 9:
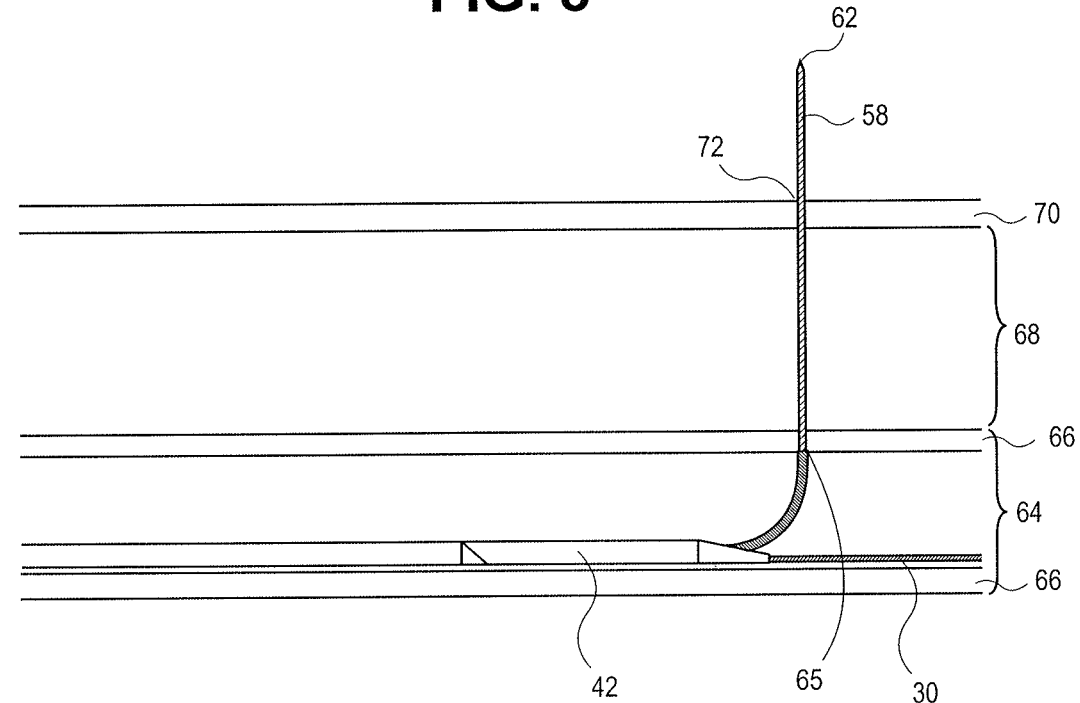
FIG. 9 is a cross-sectional schematic view of the device of FIG. 2 with the stylet advanced through the vessel wall and skin of the patient.

The cover tube 60 is then advanced out of opening 54 by moving a slide button 51 proximally in handle 44, at which point it assumes its curved shape, as shown in FIGS. 5A and 8. In some embodiments moving the slide button 51 proximally in handle 44 pushes the cover tube 60 distally. In some embodiments moving the slide button 51 proximally in handle 44 moves the catheter proximally to expose the distal end of the cover tube 60. As illustrated in FIGS. 4A and 4B the slide button 51 can engage with and be operatively connected to the catheter 42 with catheter slide 57. In some embodiments the cover tube 60 is advanced until its distal end is adjacent to the vein wall at the desired point 65 (FIG. 9). In some embodiments the cover tube 60 advances until its distal end abuts the vein wall 66 at the desired point 65, as shown in FIG. 8. The stylet 58 remains in cover tube 60.

The orientation of the extended cover tube 60 can be determined based on the orientation of the handle 44. The slide button 51 engages with the top portion 45A of the handle 44. The slide button 51, as illustrated in the figures, is substantially perpendicular to a plane defined by the opposing wings 48 that extends along a length of the handle 44, e.g. the plane defined by the area where the top portion 45A of the handle 44 contacts the bottom portion 45B of the handle 44. The cover tube 60 extends upwards from the stylet lumen 50 and is also substantially perpendicular to the plane defined by the opposing wings 48 extending along a length of the handle 44. The positioning and orientation of the cover tube 60 after it has been advanced can also be visually verified, for example using fluoroscopy prior to deploying the stylet. The stylet actuator is loaded by pulling proximally on a spring-load mechanism 52 in handle 44, as shown in FIG. 5A. When slide button 51 is in its proximal position shown in FIG. 5A, a stylet release button 53 is exposed. Depressing release button 53 advances stylet 58 distally under the action of a spring 55 to the position shown in FIGS. 5B, 6A, 7A and 9. The sharp distal tip penetrates the vein wall 66 at exit point 65, tissue 68 and skin 70 of the patient at the desired second entry point 72, as shown in FIG. 9. The distance traveled by the stylet depends on the application. For example, when the stylet is moving from the jugular vein wall through the patient's subdermal tissue and skin, the stylet may move 4 cm.

The guidewire 30 and cover tube 60 can also be used to securely position the device with a desired orientation in the vessel. The guidewire can extend from the distal end of the catheter 40 along one area of the vein wall 66. The guide tube 60 extends towards a vein wall 66 opposing the vein wall 66 that the guidewire extends along and in a substantially perpendicular orientation to the guidewire 30, as illustrated in FIG. 8. The vascular catheter 42 can be securely positioned and held in place by the support from the guidewire 30 along one side of the vein wall 66 and a point of contact 65 between the guide tube 60 and another portion of the vein wall 66.

Various sizes can be used for the cover tube 60. The configuration of the pre-formed cover tube can be varied to use different shapes. The length and pre-formed configuration of the cover tube 60 can be selected based on the size of the vessel to be accessed.

In some embodiments the cover tube 60 is not fully extended from the vascular catheter 42. For example, the cover tube 60 may not be fully extended to accommodate the specific geometry and size of vessel. In smaller diameter blood vessels there may not be enough space to fully extend the cover tube; however, the cover tube 60 and stylet 58 can properly function partially extended from the vascular catheter.

Figure 10:
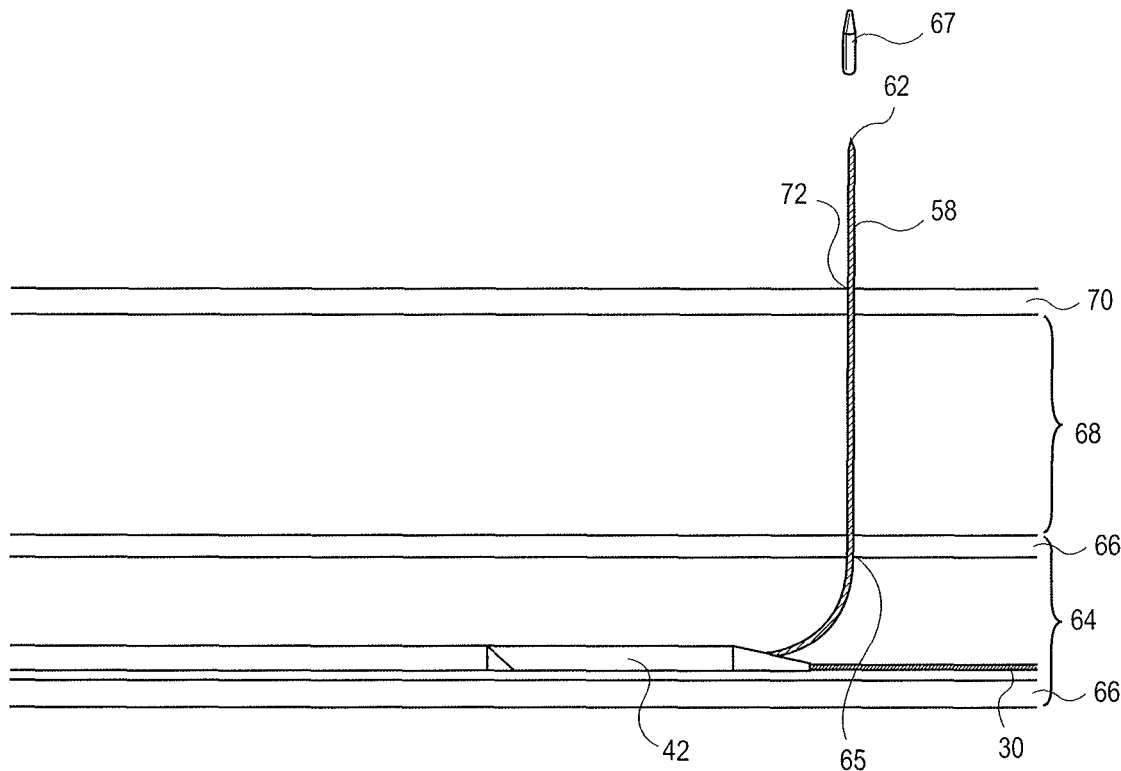
FIGS. 10-12 are cross-sectional schematic views of the device of FIG. 2 with the stylet being prepared for use in inserting another device into the vessel.
Figure 11:
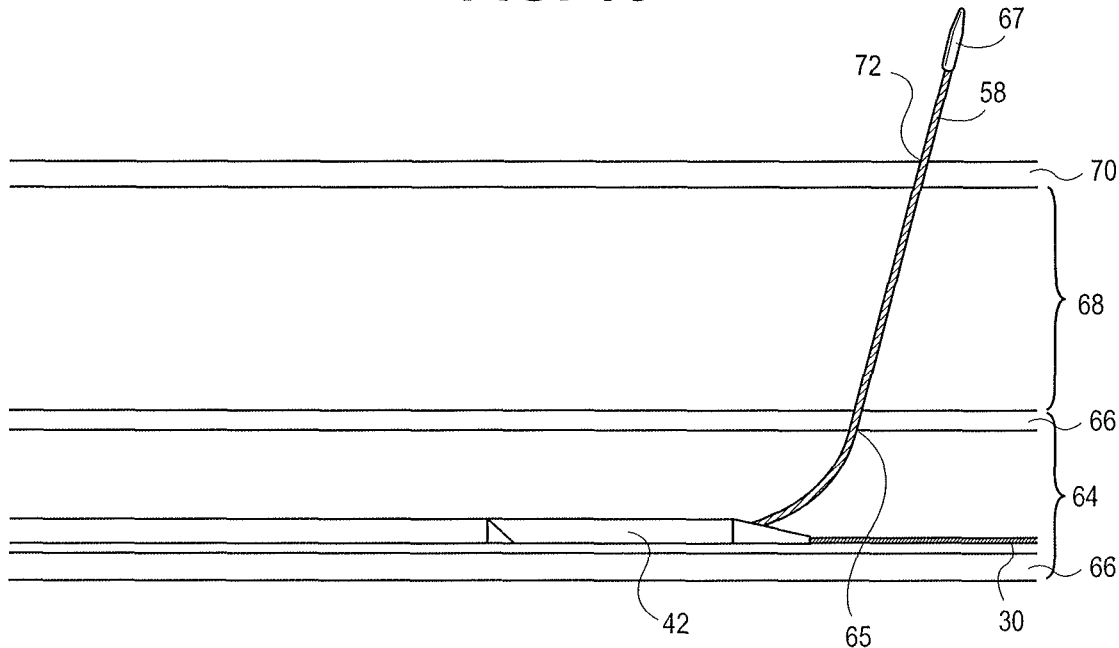
Figure 12:
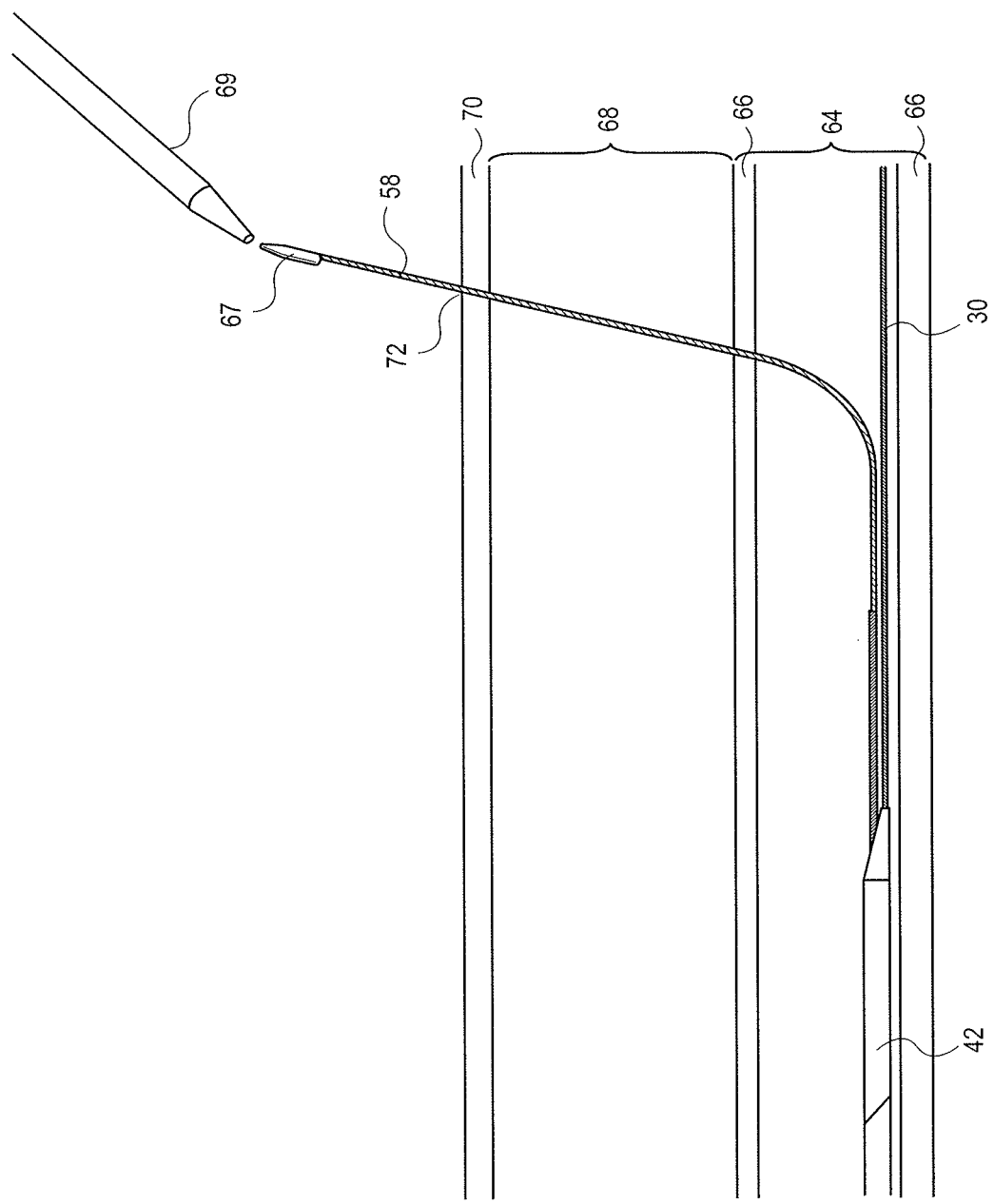
Figure 13:
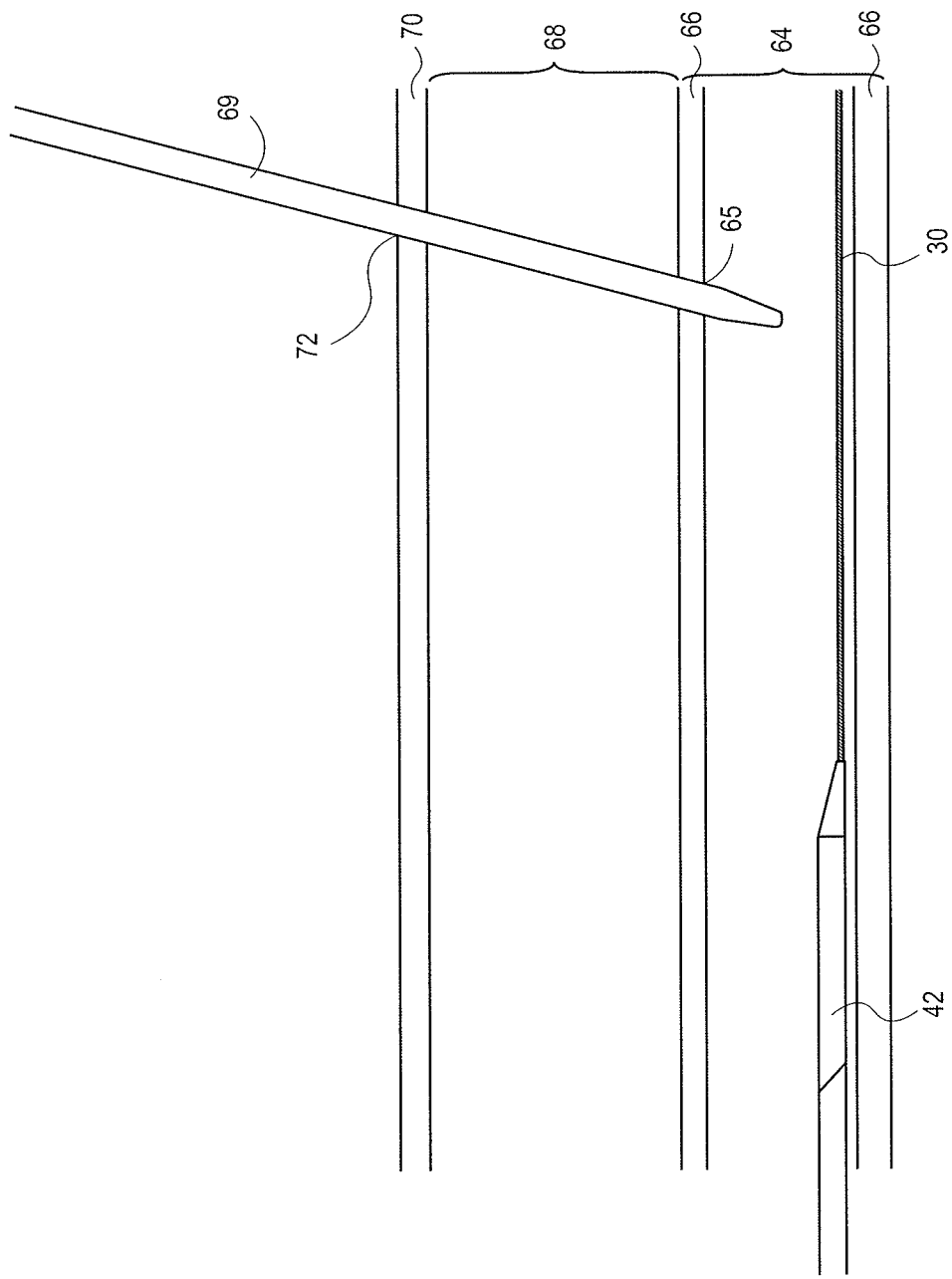
FIG. 13 is a cross-sectional schematic view of another device inserted into the vessel.
Figure 14:
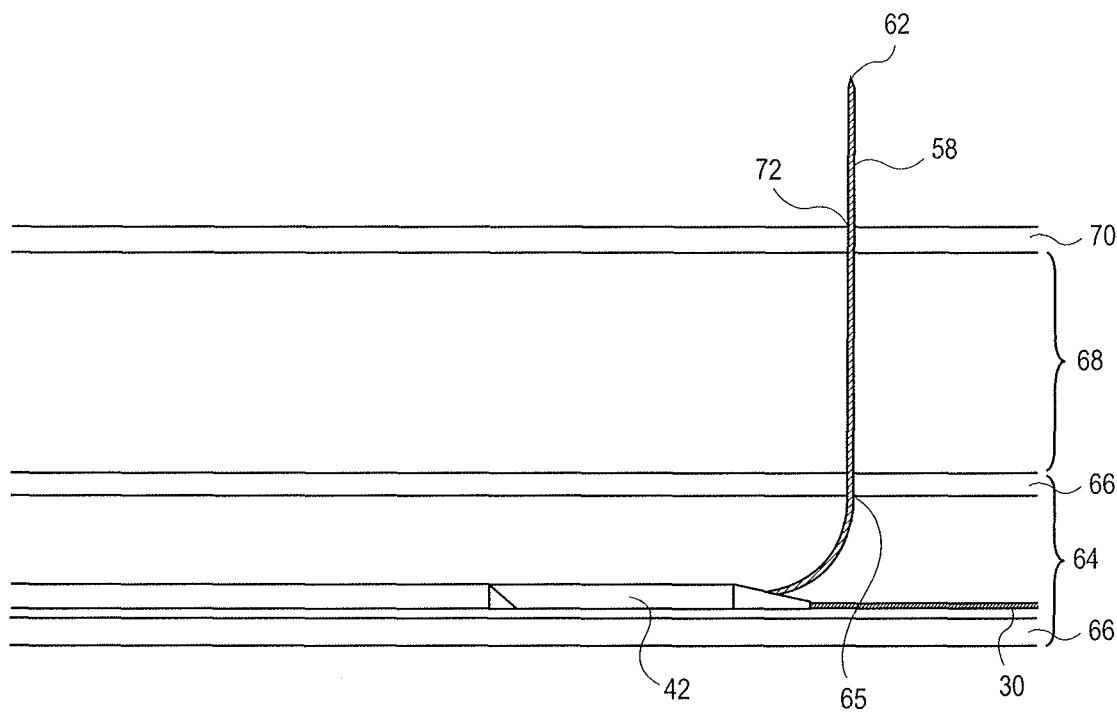
FIG. 14 is a cross-sectional schematic view of the device of FIG. 2 with the stylet cover tube advanced to a desired exit point within the vessel.
Figure 15:
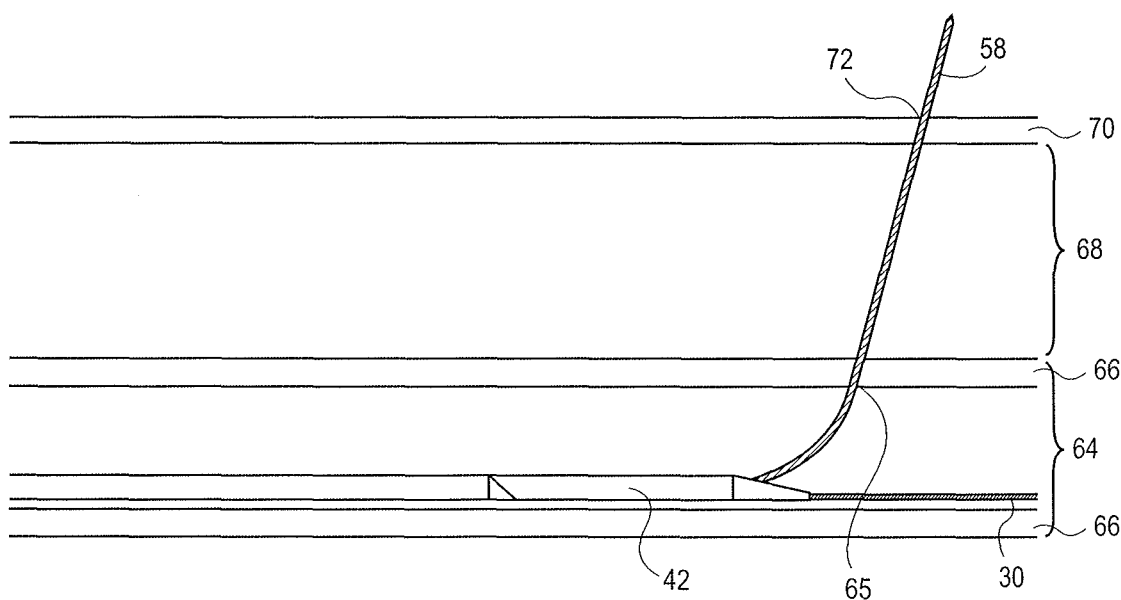
FIG. 15 is a cross-sectional schematic view of the device of FIG. 2 with the stylet advanced through the vessel wall and skin of the patient.
Figure 16:
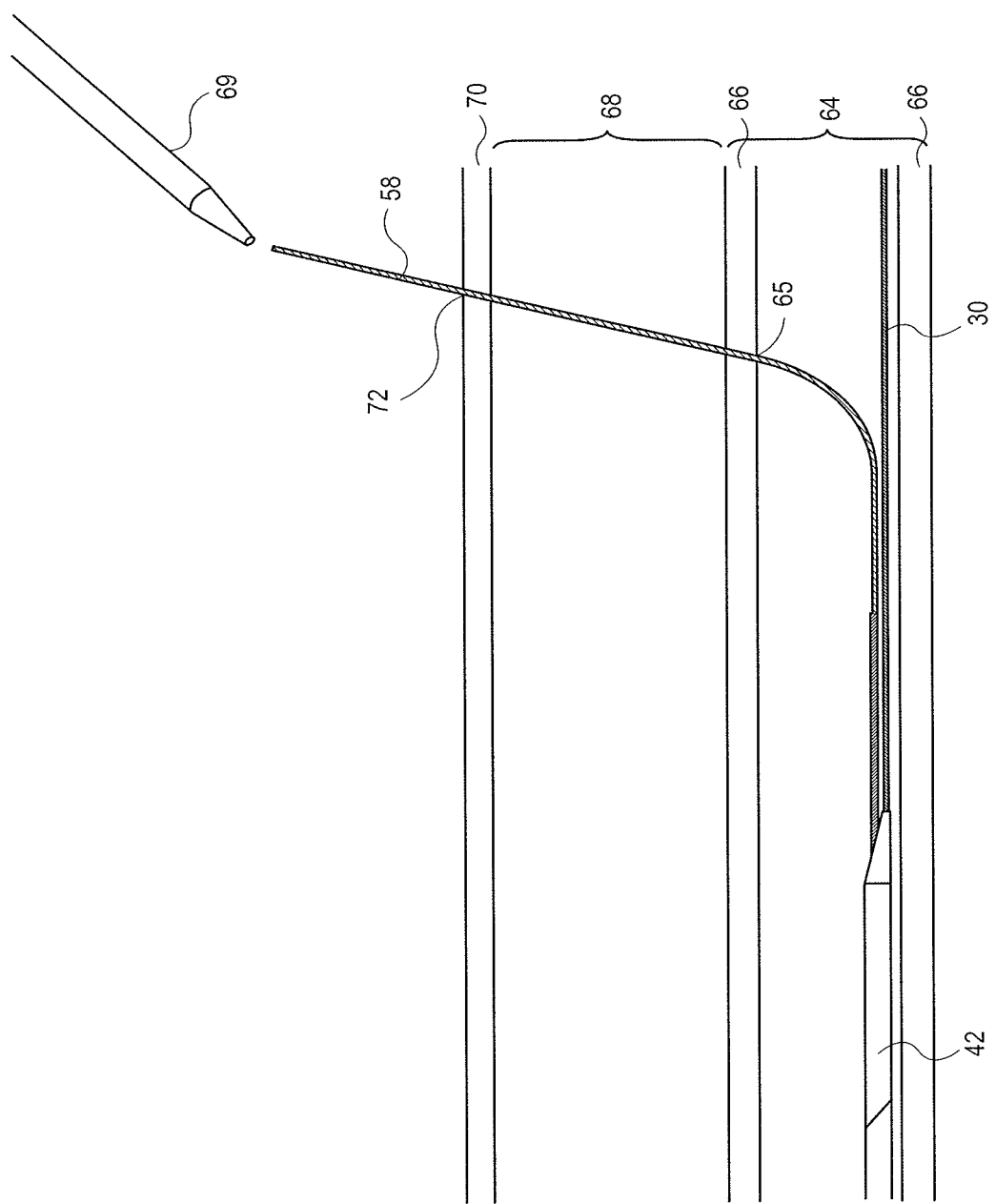
FIG. 16 is a cross-sectional schematic view of the device of FIG. 2 with the stylet being prepared for use in inserting another device into the vessel.
Figure 17:
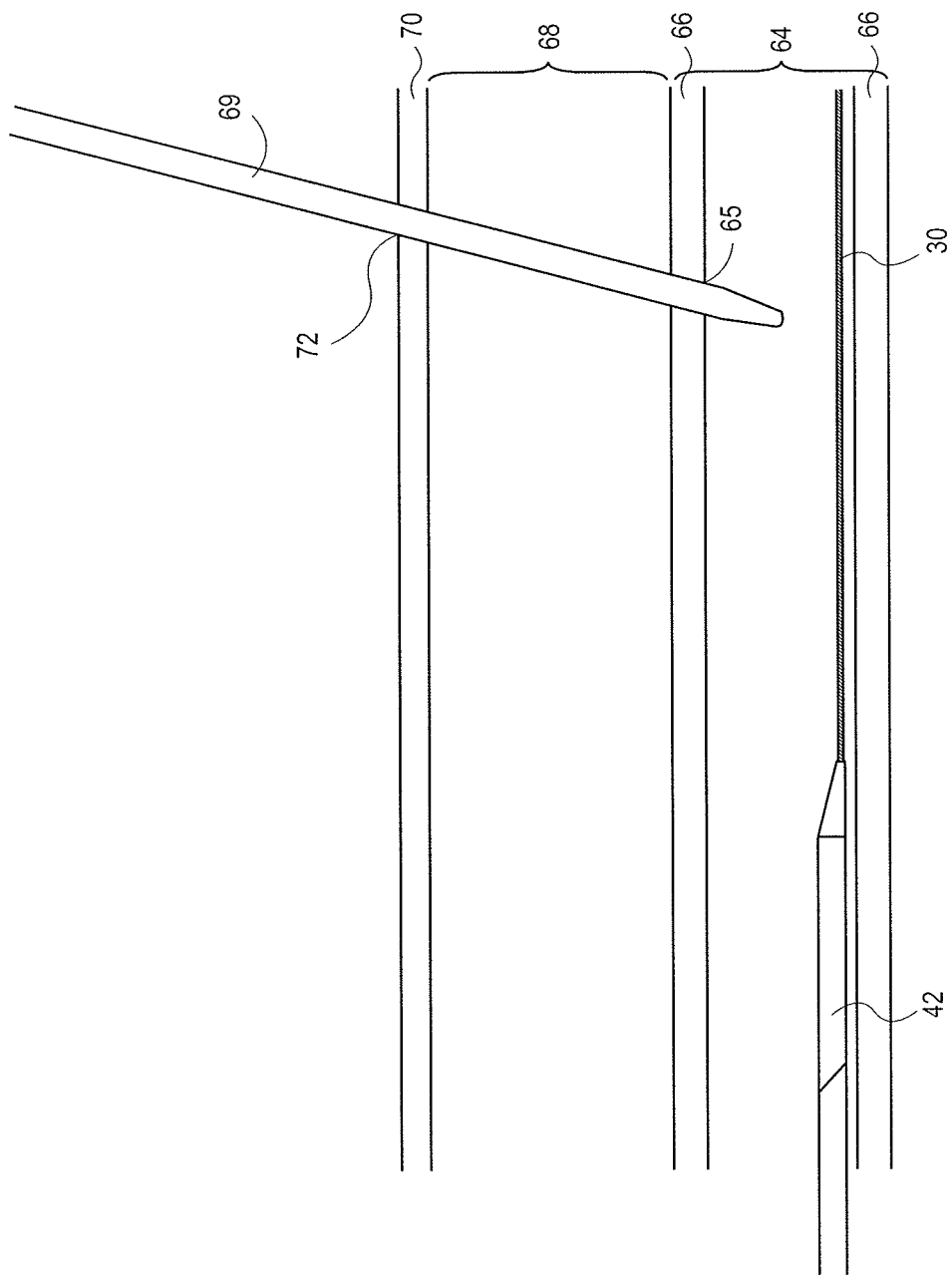
FIG. 17 is a cross-sectional schematic view of another device inserted into the vessel.

In some embodiments, a smooth tapered wire cap 67 may be placed on the distal end of stylet 58, and the stylet 58 may be tilted slightly at an angle, as shown in FIGS. 10 and 11. Catheter 42 and cover tube 60 may then be withdrawn from its femoral entry point as the physician holds stylet 58 in place. Next, the wire cap 67 is removed and then a central line or micropuncture catheter 69 may then be passed over stylet 58 into vein 64, with the stylet acting as a guidewire for micropuncture catheter 69. The stylet is then removed through either the exit location or through the femoral entry point. In some embodiments a micropuncture catheter 69 can be passed over the stylet 58 into vein 64 without the use of a wire cap as illustrated in FIGS. 14-17.

Modifications of the invention will be apparent to those skilled in the art. Different lengths and diameters of catheter, cover tube and stylet may be used depending upon the application. The length of travel of the stylet and cover tube may also be varied. As an alternative to a rapid exchange guidewire arrangement, the catheter may have a guidewire lumen extending its entire length. The guidewire, cover tube and stylet may also share the same lumen.

The devices disclosed herein can be configured to access different types of blood vessels and other hollow viscera including the bowel/intestine/gastrointestinal (GI) tract, ureter, bladder, airway, etc. In some embodiments the devices are used to access veins. In some embodiments the devices are used to access arteries. The devices can be introduced to the vascular system at a first entry point. Examples of first entry points include the femoral vein and femoral artery. The devices can be advanced to the desired target location for the formation of the second entry point. Examples of second entry points include the jugular vein, subclavian vein, carotid artery, axillary artery, and subclavian artery. The stylet can be advanced through the blood vessel wall, tissue, and skin to form the second entry point. Multiple second entry points can be formed at different locations. After formation of the second entry point a catheter or other medical device can be advanced over the stylet for access to the vascular system at the second entry point. Subsequent medical procedures can then be performed as desired.

In some application multiple entry points may be desirable. The devices disclosed herein can be used to make multiple entry points. The stylet 58 can be used to make a desired first entry point followed by introducing a device for access at the first entry point such as a catheter, as shown in FIGS. 8-17. The vascular catheter 42 can be positioned adjacent to a desired second entry point followed by advancing the stylet 58 to form a second entry point. A catheter or other device can then be used to access the vessel at the second entry point. The process can be repeated to provide vascular access at the desired number of locations.

Example 1

Figures 20A, 20B:
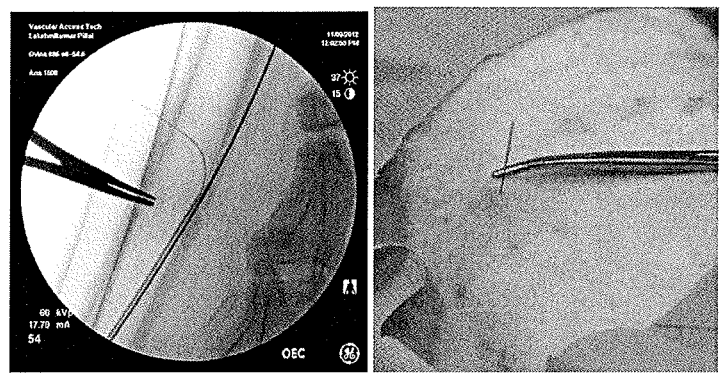
FIG. 20A is a fluoroscopic image of a device in accordance with an embodiment in an animal blood vessel.
FIG. 20B is an image of a device in accordance with an embodiment after puncturing an animal blood vessel.

Animal testing was performed using the vascular catheter devices disclosed herein. The vascular catheter was introduced to the femoral vein at a first entry point. The catheter was advanced over a guidewire to the desired target location for forming the second entry point. In one test the cover tube and stylet were deployed to puncture the vein wall, tissue, and skin at the jugular vein. An additional entry point was formed at the subclavian vein after forming the entry point in the jugular vein. In another procedure the vascular catheter was introduced into the femoral artery as the first entry point. The catheter was advanced to the carotid artery where the cover tube and stylet were deployed to form an entry point in the carotid artery. FIGS. 20A and 20B illustrate steps of the testing. FIG. 20A is a fluoroscopic image of a device in accordance with an embodiment in an animal vein. FIG. 20B is an image of a device in accordance with an embodiment, including a stylet after puncturing an animal vein.

Although the foregoing invention has been described in some detail by way of illustration and example, for purposes of clarity of understanding, it will be obvious that various alternatives, modifications and equivalents may be used and the above description should not be taken as limiting in scope of the invention which is defined in part by the appended claims.

What is claimed is:

1. A method of providing a second entry point in a vessel of a patient remote from a first entry point, the method comprising:
    deploying a vascular guidewire into the vessel from the first entry point toward the second entry point, the first entry point selected from the group consisting of: the femoral vein and femoral artery, and the second entry point selected from the group consisting of: the internal jugular vein, subclavian vein, carotid artery, axillary artery, and subclavian artery;
    inserting the guidewire into a first lumen of a vascular catheter;
    advancing the vascular catheter over the guidewire from the first entry point toward the second entry point;
    advancing a guide tube out of a distal end of a second lumen of the vascular catheter;
    directing a distal opening of the guide tube towards a wall of the vessel at the second entry point;
    advancing a stylet out of the distal end of the guide tube, through the vessel wall and skin of the patient; and
    inserting a device over the stylet and into the vessel at the second entry point.

2. The method of claim 1, wherein directing the distal opening of the guide tube towards the wall of the vessel at the second entry point includes placing the distal opening of the guide tube against the wall of the vessel at the second entry point.

3. The method of claim 1 wherein the guide tube has a preformed curve at its distal end, the step of advancing the guide tube comprising permitting the guide tube distal end to assume its preformed curve as the guide tube distal end is advanced out of the distal end of the second lumen of the vascular catheter.

4. The method of claim 1 wherein the second lumen of the vascular catheter extends in a curve at its distal end, the step of advancing the guide tube comprising engaging a camming surface in the curve of the second lumen with a distal end of the guide tube to advance the distal end of the guide tube away from a longitudinal axis of the vascular catheter and toward a wall of the vessel.

5. The method of claim 1 wherein the step of advancing the guide tube comprises moving an actuator in a handle at the proximal end of the vascular catheter.

6. The method of claim 5, wherein moving the actuator advances the guide tube relative to the second lumen of the vascular catheter.

7. The method of claim 5, wherein moving the actuator proximally retracts the vascular catheter relative to the guide tube.

8. The method of claim 1 wherein the step of advancing the stylet comprises operating a stylet actuator in a handle at the proximal end of the vascular catheter.

9. The method of claim 8 wherein the step of operating an actuator comprises releasing a spring.

10. The method of claim 9 further comprising loading the spring prior to the step of releasing the spring.

11. The method of claim 1, further comprising verifying the positioning of the guide tube after placing the distal opening of the guide tube against the wall of the vessel at the second entry point and prior to advancing the stylet.

12. The method of claim 11, wherein verifying includes using fluoroscopy to verify the position of the guide tube.

13. The method of claim 1, further comprising adjusting the orientation of the handle prior to advancing the guide tube to orient the vascular catheter such that when the guide tube is advanced out of the distal end of the second lumen, the guide tube extends from the vascular catheter towards the skin of the patient at the second entry point.

\* \* \* \* \*